United States Patent [19]

Yu et al.

[11] Patent Number: 5,817,484
[45] Date of Patent: Oct. 6, 1998

[54] THERMORESISTANT α-1-ANTITRYPSIN MUTEIN

[75] Inventors: Myeong-Hee Yu, Seoul; Ki-Sun Kwon, Taejon; Kee-Nyung Lee, Taejon; Hwa-Soo Shin, Taejon, all of Rep. of Korea

[73] Assignees: Korea Institute of Science and Technology, Seoul; Korea Green Cross Corporation, Kyongki-do, both of Rep. of Korea

[21] Appl. No.: 553,488

[22] PCT Filed: May 17, 1994

[86] PCT No.: PCT/KR94/00048

§ 371 Date: Nov. 20, 1995

§ 102(e) Date: Nov. 20, 1995

[87] PCT Pub. No.: WO94/26781

PCT Pub. Date: Nov. 24, 1994

[30] Foreign Application Priority Data

May 18, 1993 [KR] Rep. of Korea ............ 1993-8510

[51] Int. Cl.⁶ .......................... C12P 21/06; C12N 15/00; C12N 1/20; C12N 1/16

[52] U.S. Cl. .......... 435/69.2; 435/172.1; 435/252.33; 435/254.21; 435/320.1

[58] Field of Search .............. 435/69.2, 172.1, 435/252.33, 254.21, 320.1

[56] References Cited

PUBLICATIONS

Patston et al. (1990) Biol. Chem. 265, 10786–10791.

*Primary Examiner*—Rebecca E. Prouty
*Assistant Examiner*—Elizabeth Slobodyansky
*Attorney, Agent, or Firm*—Anderson, Kill & Olick, P.C.

[57] ABSTRACT

The mutagenized recombinant AT of the present invention wherein some amino acids of the amino acid sequence of a wild-type AT are replaced with another amino acid has an enhanced thermoresistance compared to the wild-type AT, while maintaining its activity. A vector containing a gene encoding the recombinant AT, a microorganism transformed with said vector and a process for producing the recombinant AT with a higher thermoresistance using said microorganism are also disclosed.

14 Claims, 8 Drawing Sheets

FIG. 1

```
  1 Glu Asp Pro Gln Gly Asp Ala Ala Gln Lys Thr Asp Thr Ser  14
 15 His His Asp Gln Asp His Pro Thr Phe Asn Lys Ile Thr Pro  28
 29 Asn Leu Ala Glu Phe Ala Phe Ser Leu Tyr Arg Gln Leu Ala  42
 43 His Gln Ser Asn Ser Thr Asn Ile Phe Phe Ser Pro Val Ser  56
 57 Ile Ala Thr Ala Phe Ala Met Leu Ser Val Gly Thr Lys Ala  70
 71 Asp Thr His* Asp Glu Ile Leu Glu Gly Leu Asn Phe Asn Leu  84
 85 Thr Glu Ile Pro Glu Ala Gln Ile His Glu Gly Phe Gln Glu  98
 99 Leu Leu His Thr Leu Asn Gln Pro Asp Ser Gln Leu Gln Leu 112
113 Thr Thr Gly Asn Gly Leu Phe Leu Ser Glu Gly Leu Lys Leu 126
127 Val Asp Lys Phe Leu Glu Asp Val Lys Lys Leu Tyr His Ser 140
141 Glu Ala Phe Thr Val Asn Phe Gly Asp Thr Glu Glu Ala Lys 154
155 Lys Gln Ile Asn Asp Tyr Val Glu Lys Gly Thr Gln Gly Lys 168
169 Ile Val Asp Leu Val Lys Glu Leu Asp Arg Asp Thr Val Phe 182
183 Ala Leu Val Asn Tyr Ile Phe Phe Lys Gly Lys Trp Glu Arg 196
197 Pro Phe Glu Val Lys Asp Thr Glu* Glu Glu Asp Phe His Val 210
211 Asp Gln Val* Thr Thr Val Lys Val Pro Met Met Lys Arg* Leu 224
225 Gly Met Phe Asn Ile Gln His Cys Lys Lys Leu Ser Ser Trp 238
239 Val Leu Leu Met Lys Tyr Leu Gly Asn Ala Thr Ala Ile Phe 252
253 Phe Leu Pro Asp Glu Gly Lys Leu Gln His Leu Glu Asn Glu 266
267 Leu Thr His Asp Ile Ile Thr Lys Phe Leu Glu Asn Glu Asp 280
281 Arg Arg Ser Ala Ser Leu His Leu Pro Lys Leu Ser Ile Thr 294
295 Gly Thr Tyr Asp Leu Lys Ser Val Leu Gly Gln Leu Gly Ile 308
309 Thr Lys Val Phe Ser Asn Gly Ala Asp Leu Ser Gly Val Thr 322
323 Glu Glu Ala Pro Leu Lys Leu Ser Lys Ala Val His Lys Ala 336
337 Val Leu Thr Ile Asp* Glu Lys Gly Thr Glu Ala Ala Gly Ala 350
351 Met Phe Leu Glu Ala Ile Pro Met Ser Ile Pro Pro Glu* Val 364
365 Lys Phe Asn Lys Pro Phe Val Phe Leu Met Ile Asp* Gln Asn 378
379 Thr Lys Ser Pro Leu Phe Met Gly Lys Val Val Asn Pro Thr 392
393 Gln Lys
```

THERMORESISTANT α-1-ANTITRYPSIN MUTEIN

FIELD OF THE INVENTION

The present invention relates to an α-1-antitrypsin (hereinafter referred as "AT") mutein with an enhanced thermoresistance and a process for the preparation thereof.

More particularly, the present invention relates to an AT mutein having an enhanced thermoresistance while maintaining its activity wherein at least one amino acid of a wild-type AT is replaced with another amino acid residue, a polynucleotide encoding said AT, a vector comprising said polynucleotide, a microorganism transformed with said vector, and a process for the preparation of AT with enhanced thermoresistance using said microorganism.

DESCRIPTION OF THE PRIOR ART

The stability of a protein is essential to maintaining its function since it determines the lifetime in vivo and storage time of the protein.

Accordingly, it is desirable for a therapeutic agent or diagnostic reagent comprising proteins to have an improved stability for the commercial practice thereof.

Since the conventional proteinous therapeutic agents isolated and purified from human body have such problems as the limitation of sources and the contamination by various infectious agents, e.g., AIDS or hepatitis virus, there have been many attempts made to produce the therapeutic agents by employing a recombinant DNA technology. However, because the proteins produced by employing the technology generally have a lower stability compared to those isolated from human body, their half-lifetime tends to be reduced markedly when administered into human body. To overcome such stability problem, two approches have been studied: one is to produce a fully glycosylated protein as in its natural form, based on the fact that the decrease in the stability is due to lack or insufficiency of the glycosylation for the protein in a microorganism; and the other is to produce a recombinant protein with an increased stability but maintaining the activity by modifying the amino acid sequence of the protein.

In this connection, it is known that the thermoresistance of a protein is closely related to its stability against denaturation (see Pace, *Trends in Biotechnology*, 8, 93–98 (1990)).

On the other hand, AT is synthesized in liver cells and then secreted into blood, and classified into serpin family together with many inhibitors of serine proteases such as trypsin, chymotrypsin, elastase, collagenase, thrombin or plasmin. AT is a glycoprotein having a molecular weight of 52 KD and physiologically serves as an inhibitor of elastase in neutrophil. In particular, it protects elastic fibers present in alveoli pulmonis from the degradation by the neutrophil elastase.

Various genetic deficiencies with regard to one's ability to produce AT are well known (see Carrell et al., *Mol. Biol. Med.*, 6, 35–42 (1982)). owing to the genetic deficiencies, the concentration of AT in blood plasma is reduced to break down a balance between a protease and its inhibitors, whereby lung loses its elasticity and there may occur emphysema (Gadek and Crystal, in *Metabolic Basis of Inherited Disease*, Stanbury et al., Eds., McGraw-Hill, N.Y., pp. 1450–1467). Further, emphysema may result from an inactivation of AT due to an excessive smoking or severe environmental pollution.

For the treatment of these disorders, therefore, the demand for AT has been increasing on a large scale; and AT isolated from human blood has been unable to meet the demand. Also, AT may be used for the treatment of acute shock syndrome (Robin W. Carrell, *Biotechnology and Genetic Engineering Reviews*, 4, 291–297 (1986)). The shock syndrome is known to be caused by the breakdown of a balance between plasma serpins and proteases due to a sudden massive release of neutrophil elastase.

The nucleotide sequence of a gene encoding AT has already been known (Long et al., *Biochemistry*, 23, 4828 (1984)); and, the AT gene has been cloned and expressed in *Escherichia coli* (Bollen et al., *FEBS Lett.*, 166, 67 (1984); Courtney et al., *Proc. Natl. Acad. Sci. USA.*, 81, 669 (1984); Tessier et al., *FEBS Lett.*, 208, 183 (1986); Johnsen et al., *Mol. Biol. Med.*, 4, 291 (1987); Sutiphong et al., *Mol. Biol. Med.*, 4, 307 (1987); Lee and Yu, *Kor. J. Biochem.*, 22, 148 (1989); and Lee et al., *Molecules and Cells*, 3, 71–74 (1993)) and in yeast (Travis et al., *J. Biol. Chem.*, 260, 4384 (1985); Rosenberg et al., *Nature*, 312, 77 (1984); Cabezon et al., *Proc. Natl. Acad. Sci. USA*, 81, 6594 (1984); Moir et al., *Gene*, 56, 209 (1987); Kim et al., *Kor. J. Biochem.*, 23, 263 (1990); and Kim et al., *Kor. J. Microbiol.*, 30, 108 (1992)).

Also, it has been reported that AT may be modified either to be an inhibitor of other serine protease than elastase or to have an increased resistance to oxidation, by replacing the methionine residue at position 358, the residue at the active site, with another amino acid residue by way of employing a site-specific mutagenesis (Rosenberg et al., *Nature*, 312, 77–80 (1984); Courtney et al., *Nature*, 313, 149–151 (1985); Barr et al., U.S. Pat. No. 4,732,973; Insley et al., U.S. Pat. No. 4,711,848). Further, it has also been reported that a nonglycosylated AT produced in yeast has a low thermoresistance in vitro and this reduction of thermoresistance closely correlates with the reduction of a half-life in vivo (Travis et al., *J. Biol. Chem.*, 260, 4384 (1985)); and, a glycosylated wild-type AT produced in yeast also has been found to have a low thermoresistance. The correlation between the structure and the function of AT has been well established by Huber and Carrell (*Biochemistry* 28, 8951–8963 (1989)).

SUMMARY OF THE INVENTION

Accordingly, it is an object of the present invention to provide a mutagenized recombinant AT ("AT mutein") having a superior thermoresistance and thermodynamic stability.

It is another object of the present invention to provide a polynucleotide encoding the AT mutein.

It is a further object of the present invention to provide a vector comprising said gene and a host cell transformed with the vector.

It is a still another object of the present invention to provide a process for producing the AT mutein having an enhanced thermoresistance by employing the transformant.

In accordance with one aspect of the present invention, there are provided AT muteins wherein at least one of the 51st, the 56th, the 59th, the 68th, the 70th, the 374th, the 381st and the 387th amino acids of a wild type AT is replaced with another amino acid.

BRIEF DESCRIPTION OF THE DRAWINGS

The above objects and features of the present invention will become apparent from the following description of preferred embodiments taken in conjunction with the accompanying drawings, in which:

FIG. 1 shows the amino acid sequence (SEQ ID NO: 1) of a representative wild-type AT;

DETAILED DESCRIPTION OF THE INVENTION

A thermoresistant AT mutein prepared in accordance with the present invention has an amino acid sequence (SEQ ID NO: 1) of a wild type human α-1-antitrypsin wherein at least one of the 51st, the 56th, the 59th, the 68th, the 70th, the 374th, the 381st and the 387th amino acids of SEQ ID NO: 1 is replaced with another amino acid. Preferred thermoresistant AT muteins are those wherein at least one of the following amino acid replacements from the wild-type AT amino acid sequence (SEQ ID NO: 1) occurs:

51st phenylalanine by cysteine, valine, leucine, isoleucine or alanine;

56th serine by alanine;

59th threonine by alanine or serine;

68th threonine by alanine;

70th alanine by glycine;

374th methionine by isoleucine, leucine or valine;

381st serine by alanine; and

387th lysine by arginine.

Among the single mutant ATs wherein only one of said amino acid replacements is made, the most preferred are those wherein the 51st residue is cysteine and wherein the 374th residue is isoleucine. These single mutant ATs have a longer (ten times or more) half-life than the wild-type AT when they are produced as a nonglycosylated form in *E. coli*; and have a much higher thermoresistance when produced as a glycosylated form in yeast.

An exemplary multiple mutant AT having two or more of said amino acid replacements may be the one wherein the 51st and the 374th residues are replaced with leucine and isoleucine, respectively; the 59th, the 68th and the 70th residues are replaced with alanine, alanine and glycine, respectively; and the 381st and the 387th residues are replaced with alanine and arginine, respectively. The multiple mutant ATs exhibit a significantly enhanced thermoresistance over the single mutant ATs. Further, if the mutant ATs are glycosylated, their thermoresistance can be more increased.

The amino acid sequence of the thermoresistant AT is identical to that of the wild-type AT except for the amino acid residue(s) replaced as above. A representative wild-type AT in the present invention may have the amino acid sequence (SEQ ID NO: 1) as shown in FIG. 1. Subtypes wherein at least one of the 101st, the 204th, the 213th, the 223rd, the 341st, the 363rd and the 376th residues in the sequence of FIG. 1 is replaced with arginine, lysine, alanine, cysteine, asparagine, lysine and glutamic acid, respectively, may be included in the category of wild-type. The wild-type AT which can be used in the present invention may be any one of the above wild-type ATs, and at least one of the first 11 successive amino acid residues of the wild-type AT may be deleted or replaced with another amino acid without a significant change in its activity.

Further, in case AT is produced in *E. coli*, Met may be added to or substituted for the N-terminal amino acid in the amino acid sequence of AT, which is also included in the "wild-type AT" within the definition of this specification.

Accordingly, AT muteins prepared on the basis of any of the amino acid sequences for the above wild-type ATs fall within the scope of the present invention. However, regardless of the deletion or addition of amino acid(s), the numbering of the amino acids in the amino acid sequence of AT is made on the basis of the numbers indicated in (SEQ ID NO: 1) FIG. 1.

The thermoresistant AT of the present invention may be produced either by a process which comprises transforming a host cell with a vector having a polynucleotide encoding the AT mutein, which is prepared by using a site specific mutagenesis, and expressing the polynucleotide from the transformant, or by a chemical synthesis of the amino acids.

A polynucleotide encoding the thermoresistant AT mutein of the present invention may be prepared either by a known chemical synthesis method or by modifying a cDNA of a wild-type AT, for example, by means of a site specific mutagenesis method.

On the other hand, it is known that several different codons encoding an amino acid may exist due to the degeneracy of a codon, and, therefore, the gene encoding the same amino acid sequence may have different nucleotide sequences.

The polynucleotide encoding the AT mutein of the present invention may be expressed by using either an appropriate procaryotic or eucaryotic expression system well known in the art (Sambrook et al., *Molecular Cloning: A Laboratory Manual*, 2nd ed., Cold Spring Harbor Laboratory Press, USA (1989)).

Expression may be carried out, in the case of a nonglycosylated AT, preferably in an *Escherichia coli* such as *E. coli* BL21 (DE3), *E. coli* JM109 (DE3) or *E. coli* NM522, and in the case of a glycosylated AT, preferably in yeast such as *Saccharomyces cerevisiae* or *Saccharomyces diastaticus*.

Suitable vector systems which may be used for the expression in *E. coli* and yeast are described by Sambrook, the supra, and by Fiers in "Proced. 8th Int. Biotechnology Symposium", *Soc. Frac. de Microbiol.*, Paris (Durand et al., eds.), pp. 680–697 (1988).

The transformation of a host cell with said expression vector may be carried out by employing any of the conventional methods (Sambrook et al., the supra; and Ito et al., *J.*

Bacteriol., 153, 163 (1983)). When E. coli is used as the host cell, a competent cell capable of taking up a vector DNA is prepared and then treated in accordance with the CaCl$_2$ method known in the art. The transformation of yeast may be carried out by way of first preparing the host cell in the form of a spaeroplast and then using a method known in the art such as those described in the above references.

In general, the host microorganism containing a desired expression vector is cultured under an optimal condition to maximize the production of the desired protein. For example, E. coli BL21 (DE3) transformed with a vector containing an ampicillin-resistant gene as a selected marker is cultivated at 37° C. in LB medium (made by dissolving 10 g of Bacto-Trypton, 5 g of Bacto-Yeast extract and 10 g of NaCl in 1 L of water) containing ampicillin. In the case of yeast, the cultivation may be carried out under an optimal growth condition as described by Sherman et al. (*Methods in Yeast Genetics,* Cold Spring Harbor, N.Y., U.S.A.).

After the cultivation of the transformant, the desired AT can be recovered and purified by using any of methods known in the art or a combination thereof.

For example, the AT mutein expressed in the transformed E. coli may be recovered by extracting from the cell culture or by disrupting the cells in accordance with any suitable method known in the protein chemistry. For the purification of the AT mutein, for example, the procedure described in Korean Patent Laid-open Publication No. 93-686 may be used. That is, the culture of the E. coli transformant is centrifuged to give the cells, which are suspended in a buffer solution containing lysozyme, and then subjected to an ultrasonication to disrupt them. Then, the disrupted cell solution is centrifuged to give a precipitate containing AT in the form of insoluble inclusion bodies. This precipitate is suspended in a buffer solution containing Triton X-100 and then recovered from the suspension. This procedure may be repeated. Thereafter, the resulting precipitate is dissolved in a buffer solution containing urea and then diluted with a potassium phosphate solution containing ethylene diamine tetracetate and mercaptoethanol. This solution is dialysed against a buffer solution containing ethylene diamine tetracetate and mercaptoethanol, and eluted through a DEAE-Sephacel column (Pharmacia LKB Biotechnology) equilibrated with the same buffer solution. The eluate is purified by FPLC over a mono-Q column (Pharmacia LKB Biotechnolgy).

When yeast is used as the host cell for the desired AT mutein to be secreted into a culture medium, the AT mutein may be isolated and purified, for example, by centrifuging the cell culture to remove the cells, concentrating the supernatant, fractionating the concentrate with ammonium sulfate, centrifuging the resulting solution to give a precipitate, carrying out a dialysis of the precipitate against a buffer solution and then eluting the resulting solution over a DEAE-Sephacel column and then a mono Q column. In case the AT mutein is accumulated within yeast cells, the cells should be disrupted prior to carrying out the above conventional purifying procedure.

The AT mutein of the present invention may serve as an inhibitor of neutrophil elastase, and, in particular, it may prevent the elastic fiber in alveoli pulmonis from being degraded by elastase. Therefore, the AT mutein can be used as a preventive and therapeutic agent of emphysema caused by genetic deficiencies or environmental pollution. Especially, the present AT mutein is highly useful due to its significantly enhanced thermoresistance.

The following Examples are intended to specifically exemplify the present invention without limiting the scope of the present invention.

In the Examples, all DNA manipulations were carried out according to the method of Sambrook et al., supra, unless otherwise mentioned. The restriction enzymes used herein were obtained from New England Biolabs in the U.S. or Boeringer Mannheim in Germany.

To determine the activity and the thermal stability of AT in the following Reference Examples and Examples, the following method was used:

The activity of AT was measured by evaluating the inhibition by AT of the elastase's activity to degrade peptides in accordance with the procedure described by Travis & Johnson in *Methods in Enzymol.,* 80, 754 (1981). Specifically, the AT's activity to inhibit elastase was evaluated by: mixing elastase and AT extract to react them, adding thereto a substrate (prepared by dissolving succinyl-alanyl-alanyl-alanyl-para-nitroanilide (SIGMA S4760) in dimethyl sulfoxide) and measuring the change of absorbency at 410 nm to determine the residual elastase activity. The thermal stability of AT was estimated by determining its activity of inhibiting elastase, using AT treated at 55° C. in case cell extract is used or at 57° to 58° C. in case a purified AT is used. As controls, a wild-type AT produced in E. coli or yeast cell and natural AT isolated and purified from human plasma were used.

Reference Example 1: Cloning of an AT gene

From the clones of a human liver cDNA library (Clontech, U.S.A.), 32 positive clones were isolated using as a probe the 50th to the 72nd nucleotides of the AT gene reported by Long et al. (*Biochemistry* 23, 4828 (1984)). 4 positive clones were obtained therefrom, using the 1150th to the 1172th nucleotides of said gene as a probe. From these clones, plasmid pUC-AT(R) was obtained, and an AT cDNA was isolated from the plasmid as a 1.3 kb fragment by the digestion with restriction endonuclease EcoRI or BamHI (see Lee & Yu, *Kor. J. Biochem.,* 22, 148 (1989)).

Reference Example 2: Expression of a wild-type E. coli recombinant AT pUC-AT(R) from the above Reference Example 1 was digested with restriction endonuclease BamHI to give a 1.3 kb fragment and the fragment was inserted into the BamHI recognition site of plasmid pET-8c (Studier and Moffatt, *J. Mol. Biol.* 189, 112 (1986)) to prepare plasmid pEAT 8. Then E. coli BL21 (DE3) was transformed with said plasmid, and AT produced therefrom was referred to as the wild-type E. coli recombinant AT. The resulting wild-type E. coli recombinant AT has an amino acid sequence in which the first residue is methionine instead of glutamic acid and the other residues are identical with those of the wild-type AT (see FIG. 1). The amino acid sequence of said wild-type recombinant AT was identified by a protein sequencing analysis using Applied Biosystem 477A. The E. coli BL21 (DE3) transformed with pEAT 8 was deposited with the Korean Collection for Type Cultures (KCTC) on Apr. 17, 1991 under the accession number of KCTC 0009BP in accordance with the terms of the Budapest Treaty on the International Recognition of the Deposit of Microorganism for the Purpose of Patent Procedure. See Korean Patent Laid-open Publication No. 93-686.

Preparation Example 1: Production of a transformant containing a randomly mutagenized gene A 1.3 kb DNA fragment obtained by the digestion of plasmid pEAT8 with BamHI was inserted into the restriction endonuclease BamHI recognition site of vector M13mpl8. A random mutagenesis was carried out using a single strand DNA obtained from the M13 clone and primers #1201 and #1212 (available from Sigma) in accordance with a modified PCR method by Eckert et al. (Eckert & Kunkel, PCR Chap. 14, *The fidelity of DNA polymerase chain reactions,* ed. by McPharson et al., Oxford Univ. Press (1991)), except that the concentration of dATP in the reaction solution was reduced to 0.1 mM, that of each of dCTP, dGTP and dTTP was 1 mM, and 10 mM magnesium chloride was added. Said PCR procedure was repeated 25 cycles. The amplified DNA was digested with restriction endonucleases BclI and BstXI to give a 770 bp fragment (from the 17th codon to the 273th codon), which was substituted for the BclI/BstXI fragment in pEAT8 of Reference Example 2. Then, *E. coli* BL21 (DE3) was transformed with the resulting plasmid and $5\times10^4$ transformant colonies having a resistance to ampicillin were obtained.

Preparation Example 2: Screening of colonies producing a thermoresistant AT

The thermoresistant AT muteins produced in *E. coli* were screened in accordance with a modified method disclosed by Coplen et al. (*Proteins; Structure, funtion and genetics,* 7, 16 (1990)). The colonies obtained in Preparation Example 1 were inoculated to 0.1 ml of a medium (prepared by dissolving 6 g of disodium phosphate, 3 g of potassium phosphate, 1 g of ammonium chloride, 2 g of glucose, 0.2 g of yeast extract and 3 g of Casamino acid in 1 L of water) containing 1 mM isopropyl β-thiogalactoside (IPTG), and then incubated overnight. To the resulting culture, 25 µl of a lysis solution (250 mM Tris, pH 8.0, 25 mM EDTA, 0.25% Triton X-100, 0.5 mg/ml of lysozyme) was added and then the culture was incubated with shaking at room temperature for one hour. Thereafter, the culture was heat-treated at 60° C. for one hour; and 25 µl of 7 nM elastase solution (SIGMA E0258) was added thereto. The reaction mixture was left at room temperature for one hour, and, then, 50 µl of 1.2 mM succinyl-alanyl-alanyl-alanyl-para-nitroanilide (SIGMA S4760) was added thereto, which was reacted at room temperature overnight. After the addition of 25 µl of sodium nitrite (0.2% dissolved in 2M HCl), the reaction mixture was left for 3 mins. 25 µl of 2% ammonium sulfate was added thereto and the solution was again left 3 mins. Then, 50 µl of N-naphtylethylene-diamine solution (0.05% in 95% ethanol) was added to develop a red color reaction. A clone which does not exhibit red color is the one producing the thermoresistant AT mutein, which was called as positive. Of the colonies prepared from Preparation Example 1, 5000 clones were screened to obtain 41 positive clones.

EXAMPLE 1

Preparation of an *E. coli* transformant expressing an AT mutein having a superior thermoresistance The elastase inhibiting activity of AT was evaluated by using a modified method described by Travis et al. (Travis & Jonhson, *Methods in Enzymol.* 80, 754 (1981)). As a reaction buffer, 50 mM Tris (pH 8.0) containing 50 mM NaCl was used, and 15 mM succinyl-alanyl-alanyl-alanyl-paranitro-anilide (SIGMA S4760) dissolved in dimethylsulfoxide was used as a substrate for elastase. An enzyme solution was prepared by dissolving elastase to the concentration of 0.3 µM in the reaction buffer solution containing 50% glycerol.

The transformed clones of Preparation Example 2 were inoculated to LB medium and incubated at 37° C. until the absorbency at 600 nm reached 0.8. 0.4 mM IPTG was added and the culture was further incubated for 3 hours. The culture was centrifuged to harvest the cells, which were suspended in a 50 mM Tris buffer solution (pH 8.0) containing 50 mM NaCl, and then subjected to an ultrasonication at 0° C. to disrupt the cells. The disrupted cell solution was centrifuged at 10,000×g for 15 mins to separate the supernatant, which was used as AT extracts.

The elastase inhibiting activity of AT was determined as follows: 10 µl of the enzyme solution, 10 to 50 µl of the AT extracts and the reaction buffer solution were mixed to make the final volume of 60 µl, and then reacted for 10 mins. After 430 µl of the reaction buffer solution and 10 µl of the substrate were added thereto, the change of absorbency at 410 nm was immediately measured for 3 mins.

To evaluate the thermoresistance, the elastase inhibiting activity of AT was measured every minute while maintaining the temperature at 55° C. An *E. coli* transformant which can produce the AT mutein having an enhanced thermoresistance compared to the wild-type recombinant AT was isolated. The transformant so desogmated *Escherichia coli* BL21 (DE3)/PEAT81 which was deposited on Mar. 19, 1993 at the Korean Collection for Type Cultures (KCTC) (address: GERI, KIST, PO Box 17, Daeduk Danji, Taejon, 305-606, (Republic of Korea) under the terms of the Budapest Treaty on the International Recognition of the Deposit of Microorganism for the Purpose of Patent Procedure under the accession number of 0077BP. The plasmid harvored in said *E. coli* BL21(DE3) is designated as pEAT81.

EXAMPLE 2

Sequencing of a nucleotide of DNA encoding the AT mutein

A 1.3 kb DNA fragment which was isolated by the digestion with BamHI of plasmid pEAT 81 obtained in Example 1 was inserted into the BamHI recognition site of a vector M13mp18. This was subjected to a sequence analysis, using $^{35}$S-dATP and Sequenase Kit (US Biochemical Co.) in accordance with a method disclosed by Sanger (Sanger et al., *Proc. Natl. Acad. Sci. USA,* 74, 5463 (1977)) to confirm that the 51th codon TTC (phenylalanine) of the DNA sequence was replaced with TGC (cysteine).

EXAMPLE 3

Isolation and purification of the AT mutein

The isolation and purification of the AT mutein was carried out using the procedure disclosed in Korean Patent Laid-open Publication No. 93-686. That is, each of the *E. coli* transformants (KCTC 0077BP and KCTC 0009BP) was inoculated into 250 ml of M9ZB medium (made by dissolving 1 g of ammonium chloride, 3 g of potassium phosphate monobasic, 6 g of sodium phosphate dibasic, 2 g of glucose, 0.2 g of yeast extract, 3 g of casamino acid in 1 L of water), and then incubated at 37° C. until the absorbency at 600 nm reached 0.8. 0.4 mM IPTG was added thereto and then the culture was further incubated for 3 hours. Each of the culture was centrifuged to harvest the cells, which were suspended in buffer solution A (50 mM NaCl, 1 mM ethylene diamine tetraacetate, 1 mM mercaptoethanol, 50 mM Tris, pH 8.0) containing 0.1 mg/ml of lysozyme and then subjected to an ultrasonication at 0° C. to disrupt the cells. Each of the suspensions was centrifuged at 10,000×g for 10 mins. to give a precipitate containing AT in the form of an insoluble inclusion bodies. Each of these precipitates was suspended in the buffer solution A comprising 0.5% Triton X-100, and then the suspension was centrifuged to recover a precipitate. This washing step was repeated once more. After solubilizing the precipitate in 5 ml of buffer solution A containing 8M urea, the resultant solution was left for 30 mins, and then diluted by the addition of 45 ml of 50 mM phosphate buffer (pH 8.0) containing 1 mM ethylene diamine tetracetate and 1 mM mercaptoethanol. After 30 mins, the diluted solution was dialysed against a 10 mM phosphate buffer solution (pH 6.5) containing 1 mM ethylene diamine tetracetate and 1 mM mercaptoethanol. The resultant dialysate was injected to a DEAE-Sephacel column (Pharmacia LKB Biotechnology) equilibrated with the dialysis buffer solution, and then eluted with the dialysis buffer solution containing NaCl of a linear concentration gradient of 0 mM to 300 mM. The eluate was again loaded on the mono-Q column (Pharmacia LKB Biotechnology) in conjunction with FPLC and eluted with the dialysis buffer solution containing NaCl having a linear concentration gradient of 0 to 200 mM to obtain a purified AT (see FIG. 2).

Figure 2:
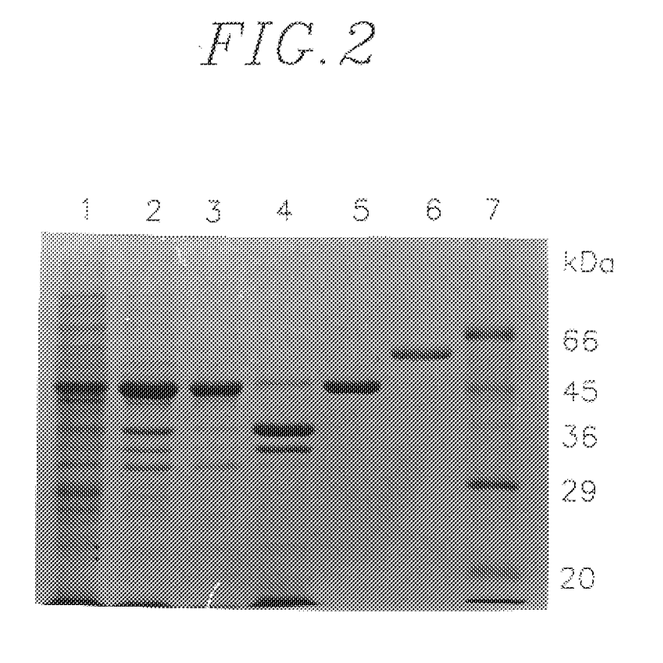
FIG. 2 is a photograph showing the result of a 12% SDS (sodium dodecyl sulfate)-polyacrylamide gel electrophoresis (SDS-PAGE) of samples taken from the steps of isolating and purifying the AT mutein from *E. coli* culture.

In FIG. 2, lane 1 is the disrupted cell extract; lane 2 shows the precipitate containing AT obtained by the centrifugation of the disrupted cells; lane 3 is the supernatant obtained from the refolding of the precipitate solubilized in urea; lane 4 is the precipitate produced during the refolding; lane 5 is the purified recombinant AT after passing through DEAE-Sephacel and mono-Q columns; lane 6 shows a human plasma AT passed through Affi-Gel Blue column and mono-Q column; and lane 7 shows the standard molecular weight proteins.

EXAMPLE 4

Characteristics of a site specific mutagenized gene and AT mutein

<4-1>: Construction of a site specific mutagenized gene

To otain a mutagenized AT in which the 51st amino acid residue is replaced with one of the other 18 amino acids than phenylalanine and cysteine, a site specific mutagenesis with an oligonucleotide (Kunkel et al., *Methods in Enzymology* 154, 367–382(1987)) was carried out. The oligonucleotide used for the mutagenesis consists of 30 bases and its sequence has been designed so that the codons adjacent to the 51st codon encode the same amino acids as the corresponding ones of the wild-type AT and the 51st codon encodes one of the 18 amino acids, as shown below:

5'-GG AGG GAA G/CNN GAT ATT AGT ACT GTT GGA C-3'(SEQ ID NO: 2)

wherein, G/C means that bases G and C are mixed in the same molar ratio; and N means that A, T, G and C are mixed in the same molar ratio.

Using *E. coli* CJ236 (dut⁻, ung⁻, Boeringer/Mannheim) as a host cell, M13 clone containing AT gene was amplified 3 times in LB medium containing 0.25 μg/ml of uridine to produce bacteriophage particles, from which a single stranded template DNA was obtained. A synthesized oligonucleotide was annealed to the template DNA. The resultant phage DNA was used to transform *E. coli* JM109(ATCC 53323) and then the mutagenized clones were selected. The sequence of the mutated M13 clones were identified as in Example 2 to confirm that the 51st residue was replaced with one of the 18 amino acids. From said mutagenized M13 clones, a RF (Replicative Form) DNA was isolated and digested with restriction endonucleases BclI and BstXI to give a 770 bp fragment, which was substituted for the BclI/BstXI fragment in plasmid pEAT8 to obtain a mutagenized AT expression vector. *E. coli* BL21 (DE3) was transformed with the vector.

<4-2>: Determination of the thermal stability of AT muteins

The cell extracts of *E. coli* producing the AT muteins were evaluated for their thermoresistance as in Example 1. The evaluation results show that the AT muteins wherein the 51st amino acid was replaced by valine, leucine, isoleucine or alanine have an increased thermal stability. Thus, after the AT muteins were purified by the same method as described in Example 3, the association constant to elastase and the thermal inactivation rate of each mutein were determined by comparing with those of the 5 human plasma AT (A9204) which was purified by passing through Affi-Gel Blue column (Bio-Rad) and then FPLC over mono-Q column. The association constant was calculated in accordance with Beatty's method (Beatty et al., *J. Biol. Chem.*, 255, 3931–3934 (1980)) as follows:

From the reaction mixture containing the same concentrations (8 nM) of elastase and AT, samples of the mixture were taken every minute for 10 mins. 1 mM succinyl-alanyl-alanyl-alanyl-p-nitroanilide (SIGMAS4760) was added as a substrate to each sample. The elastase activity of each sample was determined by measuring the absorbency at 410 nm, and then the association constant was calculated from the plot slope of reciprocal of elastase concentration vs time. As shown in Table I below, the wild-type AT and the recombinant AT mutein produced in *E. coli* have an association constant similar to that of a human plasma AT, which substantiates that the recombinant AT muteins have a normal activity to elastase.

Figure 3:
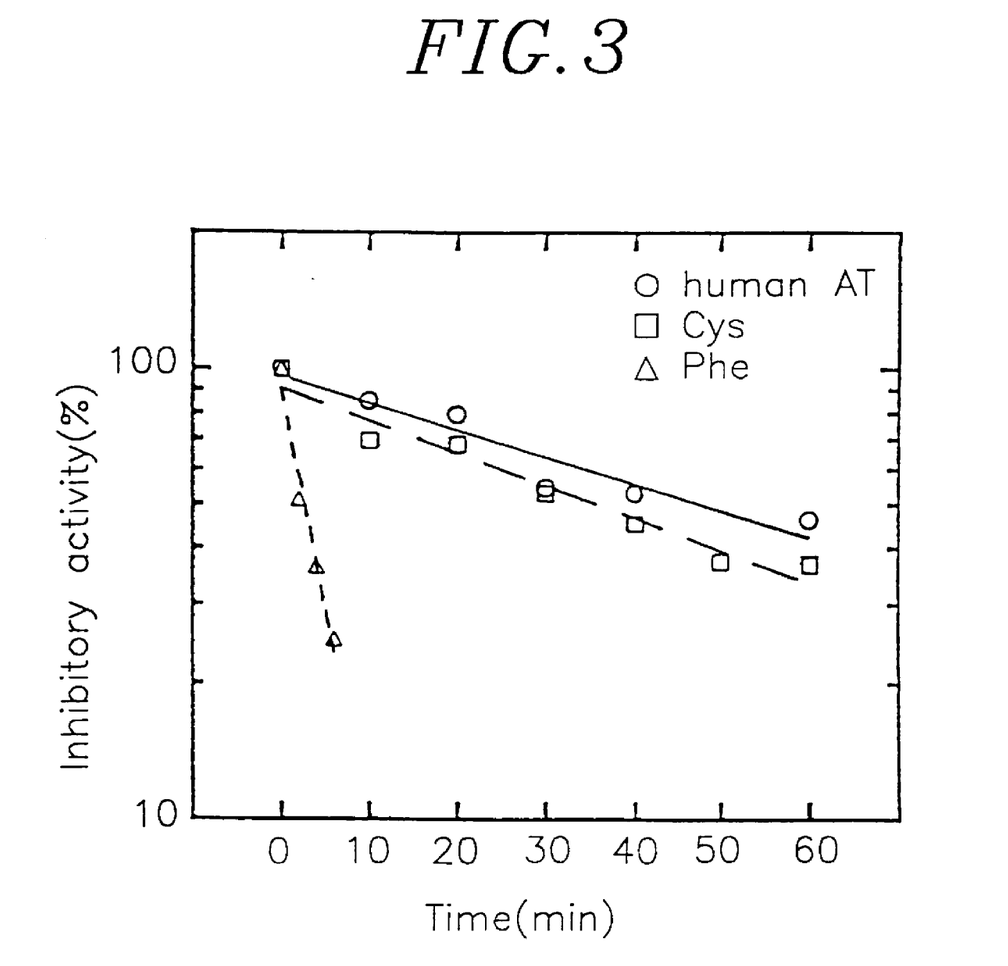
FIG. 3 is a graph showing the result of thermal inactivation experiments at 57° C. for wild-type AT and mutant AT expressed in *E. coli* and AT isolated from human plasma.

For the comparison of their thermal stability, various kinds of AT muteins were incubated at 57° C., from which samples were taken every minute. Then the remaining activity of AT muteins was determined in the same manner as described in Example 1 above and their half-life and thermal inactivation rate were calculated from the slope of the plot of a logalithmic value of the remaining activity vs time (see FIG. 3). The results are shown in Table I below.

TABLE I

Association constant, and half-life and inactivation rate at 57° C. of the mutagenized recombinant AT

| AT | the 51st codon (the 51st amino acid) | association constant ($M^{-1}$ $sec^{-1}$) | half-life (min) | inactivation rate ($sec^{-1}$) |
|---|---|---|---|---|
| wild-type recombinant AT | TTC (phenylalanine) | $1.6 \times 10^6$ | 3.1 | 0.224 |
| AT muteins | TGC (cysteine) | $1.4 \times 10^6$ | 41.7 | 0.017 |
| | CTC (luecine) | $1.9 \times 10^6$ | 40.2 | 0.017 |
| | ATC (isoleucine) | $1.6 \times 10^6$ | 33.8 | 0.021 |
| | GTC (valine) | $1.6 \times 10^6$ | 36.5 | 0.019 |
| | GCC (alanine) | $1.6 \times 10^6$ | 6.9 | 0.101 |
| Human plasma AT | | $1.7 \times 10^6$ | 49.7 | 0.014 |

As shown in the above Examples, the AT muteins possess the similar activity to that of the wild-type AT, while having an enhanced thermoresistance compared to an wild-type recombinant AT produced in *E. coli*. Especially, the AT mutein in which the 51st amino acid is replaced with cysteine exhibits the similar thermoresistance to that of human plasma AT, which is 13.5 times higher than that of the wild-type recombinant AT.

<4-3>: Decreased tendency of aggregation of the AT muteins

Figure 4:
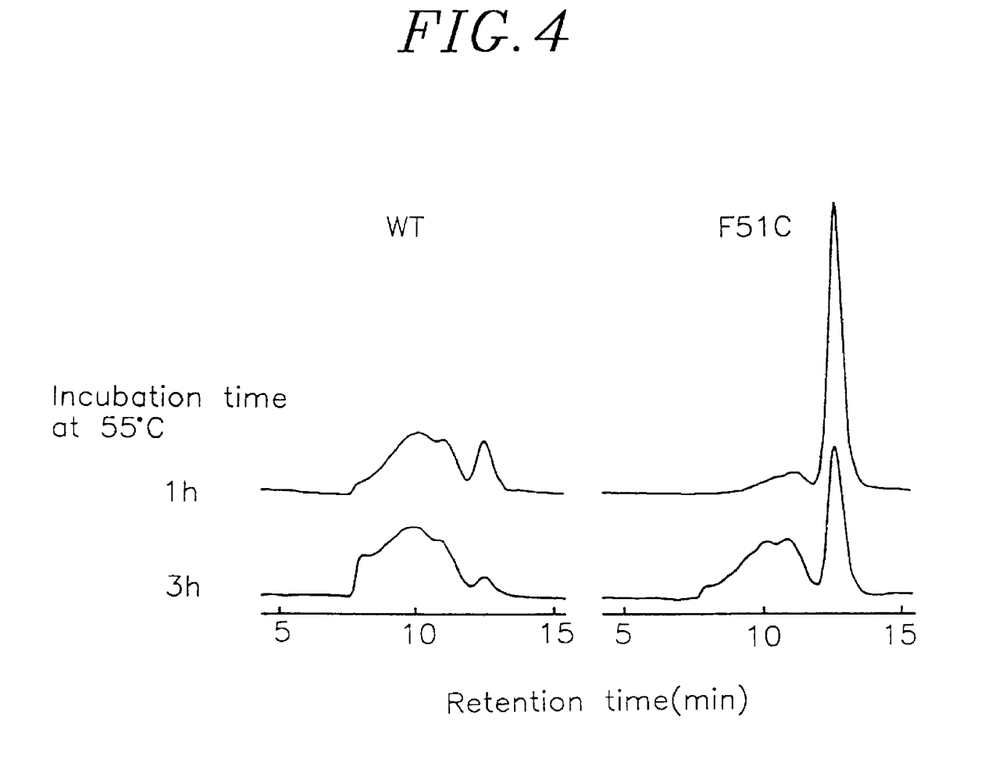
FIG. 4 is a graph depicting the result of a quantitative analysis by a gel permeation chromatography of high molecular weight proteins which are produced during storage of AT at 55° C., in order to compare the aggregations of the wild-type AT and the thermoresistant AT mutein in which the 51st amino acid residue is cysteine.

According to Lomas et al. (Lomas, D. A., et al., *Nature*, 357, 605–607 (1992); and Lomas, D. A., et al., *Biochemistry*, 32, 500–508 (1993)), AT molecules tend to be polymerized at a high temperature (above 41° C.) or under a mild denaturation condition to aggregate in a non-active form, which is known to cause a thermal inactivation. In order to compare the degree of aggregation of an AT mutein with that of a wild-type AT, the aggregation was induced and then the formation of high molecular weight proteins was evaluated by a gel permeation chromatography. More specifically, a purified AT was incubated in a concentration of 0.1 mg/ml at 55° C. for an appropriate period of time, and then fractionized by its molecular weight by means of FPLC over Superose 12 column (Pharmacia LKB Biotechnology). As shown in FIG. 4, the AT mutein of the present invention wherein the 51st amino acid is replaced with cysteine residue was found to be polymerized in a considerably lower rate compared to the wild-type AT. Accordingly, it is believed that the mutagenesis of the 51st residue of the amino acid sequence reduces the degree of inactivation of AT caused by its polymerization. In FIG. 4, the fraction eluted at 12.5 min. is the protein in an active form and the proteins eluted before that time are inactive high molecular weight proteins.

EXAMPLE 5

Preparation and Characterization of the glycosylated AT mutein

<5-1>: Construction of a vector for the expression of an AT gene in yeast

The *E. coli* expression plasmids, pEAT8 (KCTC 0009BP) and pEAT81 (KCTC 0077BP) containing a wild-type AT gene and an AT mutein gene, respectively, were digested with restriction endonucleases BamHI and SmaI, and a 1.3 Kb DNA fragment was isolated from each of the digested plasmids. Each of these fragments was inserted into the BamHI and SmaI site in plasmid pYES24 (Ahn et al., *Kor. J. Microbiol.* 30, 403(1992)). Each of the resultant plasmids was digested with BamHI, treated with a mungbean nuclease, and then ligated to construct plasmids pGAT11 (wild-type) and pGAT15 (mutant). In the plasmids, the AT gene is located after a 450 bp sequence comprising a secretion signal sequence and a part of the promoter derived from STA1 gene of *Saccharomyces diastaticus*. The construction of pGAT11 containing the wild-type AT gene has been already reported (see Song et al., *Kor. J. Microbiol.* 31, 203(1993)).

<5-2>: Preparation and cultivation of an yeast transformant

The transformation of yeast cells with the plasmids obtained in the above <5-1> was carried out in accordance with the lithium acetate method (Ito et al., *J. Bacteriol.*, 153, 163 (1983)). *Saccharomyces diastaticus* YIY345 (KCTC 1791)(Yamashita et al., *J. Bacteriol.*, 161, 574 (1985)) was employed as a host cell.

*Saccharomyces diastaticus* transformed with pGAT15 was cultured as follows: the transformant was first incubated in YNB medium (0.67% yeast nitrogen base without amino acid and 2% aqueous glucose solution) containing 20 mg/l of each of histidine and leucine at 30° C. for 16 to 18 hours, and then in YEPD medium (1% yeast extract, 2% Peptone and 2% aqueous glucose solution) for 24 hours.

The transformant is designated *Saccharomyces diastaticus* YIY345/PGAT15 which was deposited on Aug. 7, 1997 at the Korean Collection for Type Culture (KCTC) (address: KCTC, KRIBB, #190 52, Oundung, Yusong-ku, Taejon, 305-333, Republic of Korea) under the terms of the Budapest Treaty on the International Recognition of the Deposit of Microorganism for the Purpose of Patent Procedure under the accession number of 0386BP.

<5-3>: Isolation and purification of AT from the yeast culture

Each of the yeast cultures obtained from the above <5-2> was centrifuged to remove cells, and the resultant supernatant was concentrated by an ultrafiltration method (using Amicon PM30). To this concentrate was added ammonium sulfate to 60% of saturation, then the resultant solution was centrifuged at 25,000×g for 15 mins to remove the precipitate. Ammonium sulfate was added to 75% of saturation. After centrifuging the resultant solution to give a precipitate, this precipitate was dissolved in buffer solution B (10 mM Tris, 1 mM ethylenediamine tetracetate, 1 mM mercaptoethanol, pH 8.0) and dialysed against the same buffer solution. To the resultant dialysate, protamine sulfate was added to a concentration of 0.1%, which was centrifuged to remove a precipitate and dialysed against said buffer solution B. The resultant solution was purified by loading on DEAE-Sephacel (Pharmacia LKB) column equilibrated with buffer solution B, which was eluted with a linear concentration gradient of 0 to 200 mM NaCl in buffer solution B, followed by separation with mono-Q column (Pharmacia LKB) with a linear concentration gradient of 0 to 150 mM NaCl.

Figure 5:
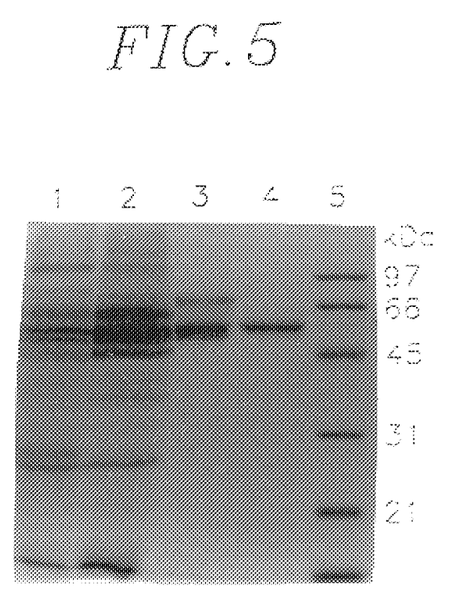
FIG. 5 is a photograph showing the result of a 12% SDS-PAGE of samples taken from the steps of isolating and purifying the AT muteins from a yeast culture.

FIG. 5 shows the result of a SDS-PAGE analysis for the samples obtained during the isolation and purification of the AT mutein from the yeast culture. Lane 1 is for the concentrate obtained after the ultrafiltration of the culture; lane 2 is for the supernatant obtained after the ammonium sulfate fractionation and the precipitation with protamine sulfate: lane 3 is for the fraction containing an active AT obtained after passing through DEAE-Sephacel column; lane 4 shows the purified AT mutein obtained after passing through mono-Q column; and lane 5 is for the standard molecular weight proteins.

<5-4>: Confirmation of glycosylation of the AT mutein produced in yeast

Figure 6:
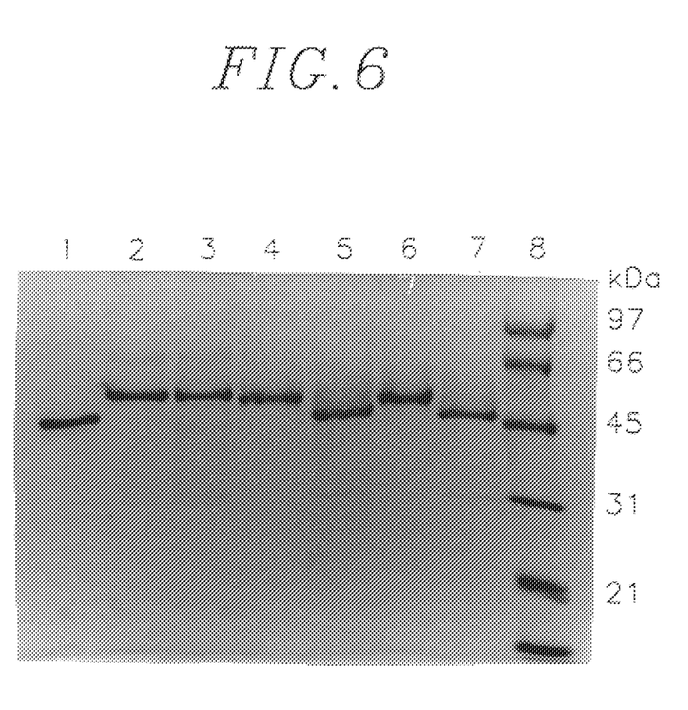
FIG. 6 is a photograph obtained by a 12% SDS-PAGE which shows the change of the molecular weight of AT after the treatment thereof with an endoglycosidase, in order to confirm whether the AT mutein produced in yeast has been glycosylated.

In order to confirm whether the AT mutein obtained from the above <5-3> is glycosylated, the purified AT mutein was treated with endoglycosidase H (New England Biolabs; hereinafter referred as "Endo H") and then subjected to SDS-PAGE. Endo H removes an N-glycosylated high-mannose type carbohydrate residue, thereby reducing the molecular weight of the glycoprotein, which can be confirmed by SDS-PAGE. Endo H does not act on a glycoprotein comprising a complex type carbohydrate produced in human. Generally, a glycoprotein secreted in yeast contains a high-mannose type carbohydrate. As shown in FIG. 6, the molecular weight of the AT mutein produced in yeast was similar to that of the human plasma AT in a glycosylated form; and after the treatment with Endo H, the molecular weight was changed to be similar to that of the nonglycosylated AT mutein having a molecular weight of 45 KD produced in E. coli. Therefore, it was confirmed that the AT mutein produced in yeast from the above <5–2> is an N-glycosylated high-mannose type glycoprotein.

In FIG. 6, lane 1 is for the nonglycosylated AT mutein expressed in E. coli; lane 2 is for the human plasma AT; lane 3 is for the human plasma AT treated with Endo H; lane 4 is for the wild-type recombinant AT produced in yeast; lane 5 is for the wild-type AT produced in yeast and treated with Endo H; lane 6 is for the AT mutein produced in yeast; lane 7 is for the AT mutein produced in yeast and treated with Endo H; and lane 8 is for the standard molecular weight proteins.

<5–5>: Characterization of the glycosylated AT mutein

Figure 7:
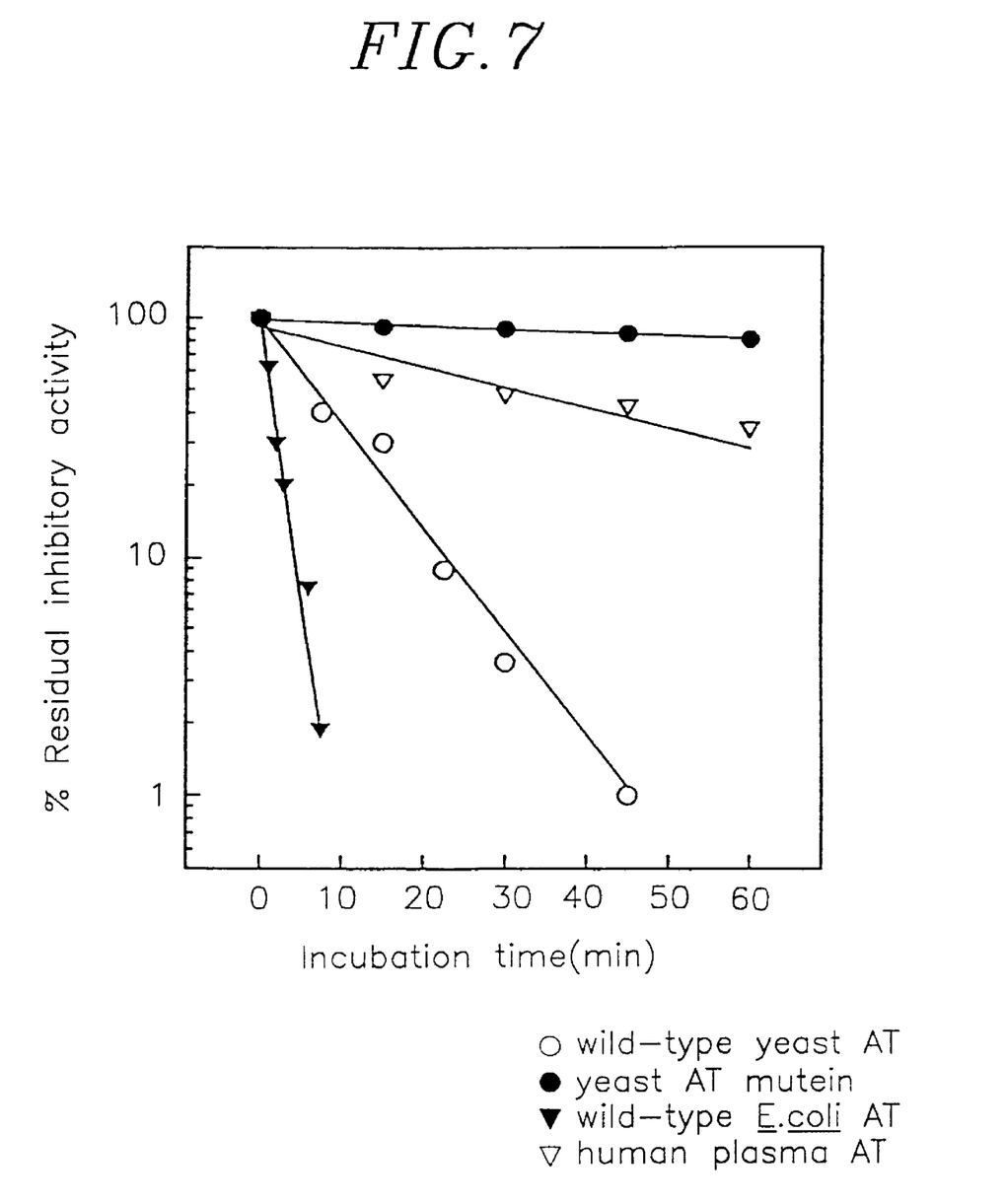
FIG. 7 is a graph depicting the comparison of thermal inactivation rates at 58° C. of AT mutein produced in yeast, the human plasma AT and the AT mutein produced in *E. coli*.

The inhibitory activity and thermal resistance at 58° C. of each of the AT muteins produced in yeast in which the 51st amino acid is replaced with cysteine and the wild-type recombinant AT purified from the above <5–3>, were determined in the same manner as in Example 4 above, and compared with those of each of the wild type E. coli recombinant AT and the human plasma AT obtained from Examples 3 and 4, respectively. The glycosylated recombinant AT exhibited the same protease inhibitory activity and an outstandingly enhanced thermal resistance compared to the wild-type AT (see FIG. 7, Table II). The wild-type recombinant AT produced in yeast had 5.3 times higher thermal resistance than that of the wild-type recombinant AT expressed in E. coli, but a lower thermoresistance than that of the human plasma AT. The glycosylated AT mutein produced in yeast, however, exhibited 31 times and 6 times higher thermal resistance, than that of the wild-type AT produced in yeast and human plasma AT, respectively.

Table II. Association constant, and half-life and inactivation rate at 58° C. of ATs produced in yeast

TABLE II

Association constant, and half-life and inactivation rate at 58° C. of ATs produced in yeast

| AT (the 51st amino acid) | association constant ($M^{-1}$ $sec^{-1}$) | half-life (min) | inactivation rate ($sec^{-1}$) |
|---|---|---|---|
| yeast AT mutein (cysteine) | $1.5 \times 10^6$ | 213.9 | 0.003 |
| wild-type yeast AT (phenylalanine) | $1.5 \times 10^6$ | 6.9 | 0.100 |
| human plasma AT (phenylalanine) | $1.7 \times 10^6$ | 35.2 | 0.020 |
| wild-type E. coli AT (phenylalanine) | $1.6 \times 10^6$ | 1.3 | 0.534 |

EXAMPLE 6

Specific site random mutagenesis using degenerated oligonucleotide and characteristics of the AT muteins In order to obtain potential thermoresistant mutants by a convergent mutagenesis at the hydrophobic core region of AT, a random mutagenesis of the hydrophobic sites adjacent to the 51st residue in the amino acid sequence of the wild-type AT was carried out by using mixed synthetic oligonucleotides. The sites selected for the mutation were the 48th to the 70th amino acid residues and the 368th to the 391st residues in the wild-type AT sequence. For the random mutagenesis, the mixed synthetic oligonucleotides were used in accordance with a method described by Hutchison (Hutchison et al., Proc. Natl. Acad. Sci. USA, 83, 710–714 (1986)). That is, each of the four (A, T, C, G) phosphoramidite solutions used for the synthesis of the oligonucleotides was contaminated with minor amounts of the other three phosphoramidite solutions. By using the contaminated solution in the synthesis of the oligonucleotide, minor bases were inserted into the resulting oligonucleotide. When these mixed synthesized oligonucleotides are used in the site-specific mutagenesis as described in Example 4 above (Kunkel, et al., Methods in Enzymology, 154, 367–382 (1987)), a random mutagenesis to a certain site can occur effectively.

In order to cover the above mentioned two sites to be mutated, the following four oligonucleotides complementary to the sequences of (a) the 48th to the 60th residues, (b) the 58th to the 70th residues, (c) the 368th to the 380th residues and (d) the 378th to the 391th residues, respectively, were synthesized and used in the mutagenesis:

(a) 5'-GGC TGT AGC GAT GCT CAC TGG GGA GAA GAA GAT ATT GGT-3'(SEQ ID NO: 3)

(b) 5'-AGC CTT GGT CCC CAG GGA GAG CAT TGC AAA GGC TGT AGC-3' (SEQ ID NO: 4)

(c) 5'-CTT GGT ATT TTG GTC AAT CAT TAA GAA GAC AAA GGG TTT-3' (SEQ ID NO: 5)

(d) 5'-GGG ATT CAC CAC TTT TCC CAT GAA GAG GGG AGA CTT GGT ATT-3' (SEQ ID NO: 6)

In this Example, for the optimal mutation frequency, each of the four phosphoramidite solutions was mixed with the other three phosphoramidites so as to be contaminated in 2.5% each. The site specific mutagenesis was carried out with the synthesized oligonucleotides by the same method as described in Example 4. The BamHI-digested mutagenized AT gene from RF DNA isolated from the obtained M13 clones was inserted into the BamHI site of expression vector pEAT8 to obtain an expression vector for the mutagenized AT gene. The thermoresistant mutants were selected by evaluating the thermal stability of the AT muteins expressed in E. coli in accordance with the screening procedure described in the above Preparation Example 2. The thermal stability at 55° C. of the AT mutein was compared with that of the E. coli wild-type recombinant AT as in Example 1 above. As a result, it was shown that the half-life of the AT mutein was increased from 2.77 to 15.73 times compared to that of the E. coli wild-type recombinant AT. The results are shown in Table III below.

TABLE III

Comparison of the thermoresistance of the AT muteins and the wild-type AT

| amino acid replacement position | replaced amino acid codon | half-life (fold) |
|---|---|---|
| E. coli wild-type recombinant AT | | 1.0 |
| the 56th | GCC (alanine) | 4.05 |
| the 59th | GCA (alanine) | 3.38 |
| the 59th | TCA (serine) | 2.97 |
| the 68th | GCC (alanine) | 4.96 |
| the 70th | GGT (glycine) | 8.78 |
| the 374th | ATT (isoleucine) | 15.73 |
| the 374th | CTG (leucine) | 7.55 |
| the 374th | GTG (valine) | 6.05 |
| the 381st | GCT (alanine) | 3.65 |
| the 387th | AGA (arginine) | 7.22 |

EXAMPLE 7

Preparation of the multiple mutant AT

Figure 8:
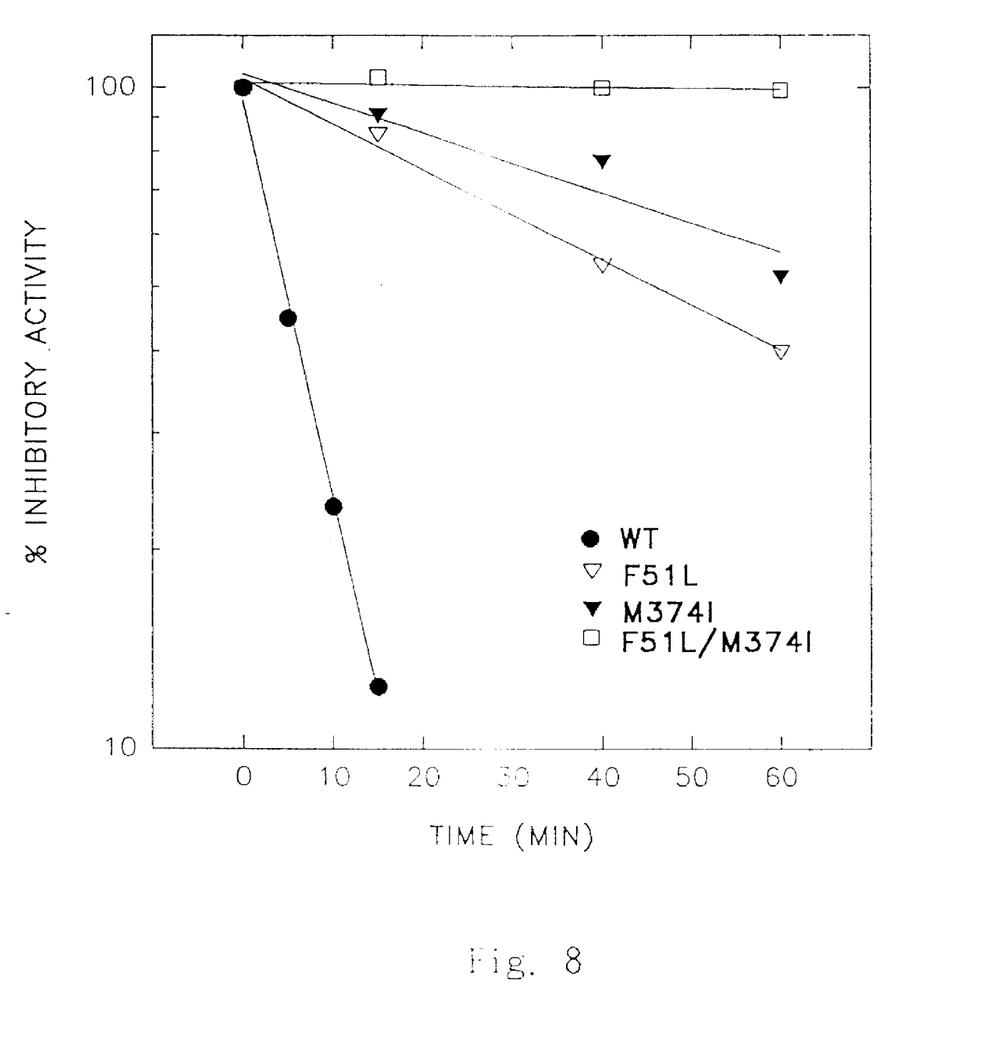
FIG. 8 is a graph showing the result of a thermal inactivation experiment for the single- and multiple mutant AT expressed in *E. coli*.

In order to obtain the mutant AT having a more enhanced thermoresistance by selectively combining the amino acid replacements in the thermoresistant AT produced in the previous Examples (Tables II & III), the multiple mutant AT in which two or more amino acids are replaced with another amino acids was produced by the site-specific mutagenesis using the oligonucleotides as described in Example 4 above. The multiple mutant AT which has two amino acid replacements wherein the 51st residue is leucine and the 374th is isoleucine, possesses a superior (300 times or more) thermoresistance than that of each of the single mutant ATs (see FIG. 8). Also, the multiple mutant AT having three amino acid replacements wherein the 59th, the 68th and the 70th residues are alanine, alanine and glycine, respectively, exhibits at least 300 times higher thermoresistance compared to the single mutant AT. FIG. 8 is a graph showing the result of the thermal inactivation experiment for the single mutant AT and multiple mutant AT expressed in *E. coli*. In FIG. 8, ● is an activity at 55° C. of the wild-type recombinant AT measured every minute in the same manner as described in Example 4 above; ▽ is that of the mutant AT in which the 51st amino acid is replaced with leucine; ▼ is that of the mutant AT wherein the 374th residue is replaced with isoleucine; and □ is that of the mutant AT in which the 51st and the 374th residues are replaced with leucine and isoleucine, respectively.

Thus, it was found that the multiple mutant additionaly enhances the thermoresistance of the single mutants. Further, it is expected that when the multiple mutant ATs are produced in a glycosylated form in yeast, their thermoresistance would be more enhanced.

While the invention has been described with respect to the above specific embodiments, it should be recognized that various modifications and changes which may be apparent to those skilled in the art to which the invention pertains may be made and also fall within the scope of the invention as defined by the claims that follow.

---

What is claimed is:

1. A human α-1-antitrypsin mutein having an enhanced thermoresistance which has an amino acid sequence (SEQ ID NO: 1) of a wild type human α-1-antitrypsin, wherein at least one of the 51st, the 56th, the 59th, the 68th, the 70th, the 374th, the 381st, and the 387th amino acids of SEQ ID NO: 1 is replaced with another amino acid.

2. The human α-1-antitrypsin mutein of claim 1 wherein at least one of the following amino acid replacements occurs:

51st phenylalanine by cysteine, valine, leucine, isoleucine or alanine;
   56th serine by alanine;
   59th threonine by alanine or serine;
   68th threonine by alanine;
   70th alanine by glycine;
   374th methionine by isoleucine, leucine or valine;
   381st serine by alanine; and
   387th lysine by arginine.

3. The human α-1-antitrypsin mutein of claim 1 wherein at least one of the 11 successive amino acids from the N-terminus is deleted or replaced with another amino acid.

4. The human α-1-antitrypsin mutein of claim 1 which is glycosylated.

5. The human α-1-antitrypsin mutein of claim 1 wherein the 51st phenylalanine and the 374th methionine of the wild-type human α-1-antitrypsin are replaced with leucine and isoleucine, respectively.

6. The human α-1-antitrypsin mutein of claim 1 wherein the 59th threonine, the 68th threonine and the 70th alanine of the wild-type human α-1-antitrypsin are replaced with alanine, alanine and glycine, respectively.

7. A polynucleotide encoding the human α-1-antitrypsin mutein according to claim 1.

8. An expression vector containing the polynucleotide according to claim 7.

9. The vector of claim 8 which is pEAT81 or pGAT15.

10. A microorganism which is transformed with an expression vector containing the polynucleotide according to claim 7.

11. The microorganism transformant of claim 10 which is prepared by transforming *Escherichia coli* BL21(DE3) with pEAT81, deposited under KCTC 0077BP.

12. The microorganism of claim 10 which is prepared by transforming *Saccharomyces diastaticus* YIY345 with pGAT15, deposited under KCTC 0368BP.

13. A process for preparing the human α-1-antitrypsin mutein according to claim 1 having an enhanced thermoresistance which comprises culturing the microorganism of claim 10 under an appropriate condition and isolating the produced AT mutein from the culture.

14. The process of claim 13 wherein a glycosylated human α-1-antitrypsin mutein is prepared by culturing *Saccharomyces diastaticus* YIY 345 transformed with pGAT15 and isolating the produced mutein from the culture.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 394 amino acids
        ( B ) TYPE: amino acid
        ( D ) TOPOLOGY: linear     ( i i ) MOLECULE TYPE: protein     ( i x ) FEATURE:
        ( D ) OTHER INFORMATION: wild type human alpha-1-antitrypsin     ( x i ) SEQUENCE DESCRIPTION: SEQ ID NO: 1:

```
Glu  Asp  Pro  Gln  Gly  Asp  Ala  Ala  Gln  Lys  Thr  Asp  Thr  Ser  His
 1                    5                        10                       15

His  Asp  Gln  Asp  His  Pro  Thr  Phe  Asn  Lys  Ile  Thr  Pro  Asn  Leu
                     20                        25                       30

Ala  Glu  Phe  Ala  Phe  Ser  Leu  Tyr  Arg  Gln  Leu  Ala  His  Gln  Ser
                     35                        40                       45

Asn  Ser  Thr  Asn  Ile  Phe  Phe  Ser  Pro  Val  Ser  Ile  Ala  Thr  Ala
                     50                        55                       60

Phe  Ala  Met  Leu  Ser  Val  Gly  Thr  Lys  Ala  Asp  Thr  His  Asp  Glu
                     65                        70                       75

Ile  Leu  Glu  Gly  Leu  Asn  Phe  Asn  Leu  Thr  Glu  Ile  Pro  Glu  Ala
                     80                        85                       90

Gln  Ile  His  Glu  Gly  Phe  Gln  Glu  Leu  Leu  His  Thr  Leu  Asn  Gln
                     95                        100                      105

Pro  Asp  Ser  Gln  Leu  Gln  Leu  Thr  Thr  Gly  Asn  Gly  Leu  Phe  Leu
                     110                       115                      120

Ser  Glu  Gly  Leu  Lys  Leu  Val  Asp  Lys  Phe  Leu  Glu  Asp  Val  Lys
                     125                       130                      135

Lys  Leu  Tyr  His  Ser  Glu  Ala  Phe  Thr  Val  Asn  Phe  Gly  Asp  Thr
                     140                       145                      150
```

-continued

| | | | | | | | | | | | | |
|---|---|---|---|---|---|---|---|---|---|---|---|---|
| Glu | Glu | Ala | Lys | Lys<br>155 | Gln | Ile | Asn | Asp | Tyr<br>160 | Val | Glu | Lys | Gly | Thr<br>165 |
| Gln | Gly | Lys | Ile | Val<br>170 | Asp | Leu | Val | Lys | Glu<br>175 | Leu | Asp | Arg | Asp | Thr<br>180 |
| Val | Phe | Ala | Leu | Val<br>185 | Asn | Tyr | Ile | Phe | Phe<br>190 | Lys | Gly | Lys | Trp | Glu<br>195 |
| Arg | Pro | Phe | Glu | Val<br>200 | Lys | Asp | Thr | Glu | Glu<br>205 | Glu | Asp | Phe | His | Val<br>210 |
| Asp | Gln | Val | Thr | Thr<br>215 | Val | Lys | Val | Pro | Met<br>220 | Met | Lys | Arg | Leu | Gly<br>225 |
| Met | Phe | Asn | Ile | Gln<br>230 | His | Cys | Lys | Lys | Leu<br>235 | Ser | Ser | Trp | Val | Leu<br>240 |
| Leu | Met | Lys | Tyr | Leu<br>245 | Gly | Asn | Ala | Thr | Ala<br>250 | Ile | Phe | Phe | Leu | Pro<br>255 |
| Asp | Glu | Gly | Lys | Leu<br>260 | Gln | His | Leu | Glu | Asn<br>265 | Glu | Leu | Thr | His | Asp<br>270 |
| Ile | Ile | Thr | Lys | Phe<br>275 | Leu | Glu | Asn | Glu | Asp<br>280 | Arg | Arg | Ser | Ala | Ser<br>285 |
| Leu | His | Leu | Pro | Lys<br>290 | Leu | Ser | Ile | Thr | Gly<br>295 | Thr | Tyr | Asp | Leu | Lys<br>300 |
| Ser | Val | Leu | Gly | Gln<br>305 | Leu | Gly | Ile | Thr | Lys<br>310 | Val | Phe | Ser | Asn | Gly<br>315 |
| Ala | Asp | Leu | Ser | Gly<br>320 | Val | Thr | Glu | Glu | Ala<br>325 | Pro | Leu | Lys | Leu | Ser<br>330 |
| Lys | Ala | Val | His | Lys<br>335 | Ala | Val | Leu | Thr | Ile<br>340 | Asp | Glu | Lys | Gly | Thr<br>345 |
| Glu | Ala | Ala | Gly | Ala<br>350 | Met | Phe | Leu | Glu | Ala<br>355 | Ile | Pro | Met | Ser | Ile<br>360 |
| Pro | Pro | Glu | Val | Lys<br>365 | Phe | Asn | Lys | Pro | Phe<br>370 | Val | Phe | Leu | Met | Ile<br>375 |
| Asp | Gln | Asn | Thr | Lys<br>380 | Ser | Pro | Leu | Phe | Met<br>385 | Gly | Lys | Val | Val | Asn<br>390 |
| Pro | Thr | Gln | Lys | | | | | | | | | | | |

( 2 ) INFORMATION FOR SEQ ID NO: 2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: DNA     ( i x ) FEATURE:
        ( D ) OTHER INFORMATION: oligonucleotide     ( x i ) SEQUENCE DESCRIPTION: SEQ ID NO: 2:

GGAGGGAASN NGATATTAGT ACTGTTGGAC        30

( 2 ) INFORMATION FOR SEQ ID NO: 3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     ( i i ) MOLECULE TYPE: DNA     ( i x ) FEATURE:

(D) OTHER INFORMATION: oligonucleotide (xi) SEQUENCE DESCRIPTION: SEQ ID NO: 3:

GGCTGTAGCG ATGCTCACTG GGGAGAAGAA GATATTGGT 39

(2) INFORMATION FOR SEQ ID NO: 4:

(i) SEQUENCE CHARACTERISTICS:
      (A) LENGTH: 39 base pairs
      (B) TYPE: nucleic acid
      (C) STRANDEDNESS: single
      (D) TOPOLOGY: linear    (ii) MOLECULE TYPE: DNA    (ix) FEATURE:
      (D) OTHER INFORMATION: oligonucleotide    (xi) SEQUENCE DESCRIPTION: SEQ ID NO: 4:

AGCCTTGGTC CCCAGGGAGA GCATTGCAAA GGCTGTAGC 39

(2) INFORMATION FOR SEQ ID NO: 5:

(i) SEQUENCE CHARACTERISTICS:
      (A) LENGTH: 39 base pairs
      (B) TYPE: nucleic acid
      (C) STRANDEDNESS: single
      (D) TOPOLOGY: linear    (ii) MOLECULE TYPE: DNA    (ix) FEATURE:
      (D) OTHER INFORMATION: oligonucleotide    (xi) SEQUENCE DESCRIPTION: SEQ ID NO: 5:

CTTGGTATTT TGGTCAATCA TTAAGAAGAC AAAGGGTTT 39

(2) INFORMATION FOR SEQ ID NO: 6:

(i) SEQUENCE CHARACTERISTICS:
      (A) LENGTH: 42 base pairs
      (B) TYPE: nucleic acid
      (C) STRANDEDNESS: single
      (D) TOPOLOGY: linear    (ii) MOLECULE TYPE: DNA    (ix) FEATURE:
      (D) OTHER INFORMATION: oligonucleotide    (xi) SEQUENCE DESCRIPTION: SEQ ID NO: 6:

GGGATTCACC ACTTTTCCCA TGAAGAGGGG AGACTTGGTA TT 42